United States Patent [19]

Smirnov et al.

[11] Patent Number: 4,565,805

[45] Date of Patent: Jan. 21, 1986

[54] PHARMACEUTICAL PREPARATION FOR THE TREATMENT OF PEPTIC ULCER

[76] Inventors: Vladimir N. Smirnov, Juzhinsky pereulok, 3, kv. 7; Mikhail I. Titov, Kuntsevskaya ulitsa, 1/5, kv. 368; Zhanna D. Bespalova, Kuntsevskaya ulitsa, 1/5, kv. 229; Andrei A. Azmuko, ulitsa Ukhtomskaya, 13, kv. 21; Tatyana R. Sax, ulitsa Marshala Timoshenko, 34, kv. 115; Oleg S. Medvedev, Berezhkovskaya naberezhnaya, 14, kv. 32; Nadezhda I. Rozhanskaya, ulitsa Dmitria Ulyanova, 4, korpus 2, kv. 226; Vsevolod G. Smagin, ulitsa Vesnina, 30, kv. 17; Valentin A. Vinogradov, Khoroshevskoe shosse, 34, kv. 38; Vladimir M. Polonsky, prospekt Mira, 91, korpus 3, kv. 386; Sergei A. Bulgakov, Ruzheiny pereulok, 4, kv. 17; Vladimir N. Ivanov, Kavkazsky bulvar, 38, kv. 18, all of Moscow, U.S.S.R.

[21] Appl. No.: 633,909

[22] PCT Filed: Oct. 31, 1983

[86] PCT No.: PCT/SU83/00039

§ 371 Date: Jul. 20, 1984

§ 102(e) Date: Jul. 20, 1984

[87] PCT Pub. No.: WO84/02470

PCT Pub. Date: Jul. 5, 1984

[51] Int. Cl.$^4$ .................... A61K 37/00; C07C 103/52
[52] U.S. Cl. ................. 514/17; 260/112.5 R
[58] Field of Search ............... 260/112.5 R, 112.5 E; 514/17

[56] References Cited

PUBLICATIONS

Chankin et al., *Proc. Natl. Acad. Sci.*, USA, 78, No. 10, 6543–6547 (1981).

*Primary Examiner*—Delbert R. Phillips
*Assistant Examiner*—F. T. Moezie
*Attorney, Agent, or Firm*—Burgess, Ryan & Wayne

[57] ABSTRACT

A pharmaceutical preparation or the treatment of peptic ulcer comprising an active principle, notably a peptide of the following structure:

Tyr-D-Ala-Gly-Phe-Leu-Arg and a pharmaceutically acceptable vehicle.

6 Claims, No Drawings

PHARMACEUTICAL PREPARATION FOR THE TREATMENT OF PEPTIC ULCER

FIELD OF THE INVENTION

The present invention relates to the art of pharmacology and, more specifically, to a novel pharmaceutical preparation for the treatment of peptic ulcer.

BACKGROUND OF THE INVENTION

It is known in the art that various preparations can be employed in gastroenterology for the treatment of peptic ulcer such as anticholinergic agents—atropine, glycopyrolate, antacids—aluminium hydroxide, calcium carbonate and the like (cf. Cristensen et al., Gastroenterology. 1977, v. 73, pp. 1170-1178).

The antiulcerous effect of anticholinergic preparations and antacids is based on their ability of lowering acidity of the gastric juice, wherefore these preparations are administered in high doses. The use of such doses of the preparations is accompanied by the development of numerous side effects.

At present cymethidin is considered to be the most effective preparation for the treatment of peptic ulcer; its effect is based on blocking $H_2$-receptors of histamine (cf. Brimblecombe et al., Gastroenterology, 1978, v. 74, pp. 339-347). As the same time cymethidin gives a number of side effects: it causes endocrinous changes; being an antiandrogen, it affects metabolism of pharmaceutical preparations in liver.

Described in the literature is a peptide having the following structure: Tyr-D-Ala-Gly-Phe-Leu-Arg (Chavkin, Goldstein, Proc. Natl. Acad. Sci. USA. 1981, v. 78, pp. 6543-6547). However, its possible applications have not been specified.

DISCLOSURE OF THE INVENTION

The pharmaceutical preparation according to the present invention is novel and hitherto unknown from the literature.

The present invention is directed to the utilization of a novel pharmaceutical preparation for the treatment of peptic ulcer which provides an accelerating effect on processes of ulcer healing, has a low toxicity, a broad spectrum of therapeutic action and causes no side effects.

This object is accomplished by the use of a pharmaceutical preparation for the treatment of peptic ulcer comprising an active ingredient and a pharmaceutically acceptable vehicle which contains, as the active ingredient, a peptide of the following structure:

Tyr-D-Ala-Gly-Phe-Leu-Arg.

The preparation according to the present invention can be administered in diverse pharmaceutical forms (injections, solutions, tablets and the like). It is preferable to use the preparation according to the present invention in the form of injectable solutions with a content of the active principle of 0.1-0.5% by weight. As the pharmaceutically acceptable vehicle the preparation preferably contains bidistilled water or a 0.9% aqueous solution of sodium chloride.

The preparation according to the present invention in the form of tablets preferably contains the active ingredient in an amount of 10 to 50 mg per tablet. As the pharmaceutically acceptable vehicle for tablets it preferably contains starch, glucose or lactose.

The preparation of this invention provides an accelerating effect on processes of healing of peptic ulcer of the duodenum and stomach. Physiological effects of the preparation according to the present invention are revealed in acceleration of scarring at the site of ulcer.

The preparation is characterized by a low toxicity, a small single dose, and an effective therapeutic action. The preparation is adapted for the treatment of peptic ulcer.

BEST MODE OF CARRYING OUT THE INVENTION

The preparation for the treatment of peptic ulcer according to the present invention was experimentally tested on animals and clinically on humans.

The effectiveness of the preparation was studied on an experimental model of a cystamine duodenal ulcer in rats and on a model of gastric ulcers in rats caused by immobilization for 24 hours.

Duodenal ulcers were induced by means of a subcutaneous administration of cystamine hydrochloride in a single dose of 350 mg/kg.

The preparation according to the present invention was also subcutaneously administered twice a day in a physiological solution. In the experiments 350 male rats of the V-starline of a 150-200 g mass were used. The animals were slaughtered by decapitation 48 hours after administration of cystamine. The state of the mucous membrane of the duodenum was visually assessed by means of a binocular magnifying glass (x5) using the following scale: 0—the mucous membrane is intact, 2—single ulcer, 3—plural ulcers, 4—penetrating ulcers. The severity of injury in each group of animals was assessed by an average point figure; also calculated was the frequency of injury (the number of animals with ulcers/the number of animals in the group). For a total evaluation an ulcer index was used which was calculated by the formula:

Index = Severity + Doubled Frequency.

The results obtained for administration of different doses of the preparation according to the present invention are shown in the following Table 1.

TABLE 1

Effect of the preparation according to the present invention on the development of duodenal ulcers in rats

| Dose of the preparation (μg/kg) 1 | Number of rats 2 | Characteristics | | |
|---|---|---|---|---|
| | | Severity 3 | Frequency 4 | Index 5 |
| Control | 60 | 1.78 ± 0.17 | 0.66 | 3.10 |
| 1 | 20 | 0.89 ± 0.24* | 0.44 | 1.70 |
| 5 | 20 | 0.57 ± 0.25* | 0.29* | 1.15 |
| 12 | 40 | 0.28 ± 0.14* | 0.13* | 0.54 |
| 50 | 20 | 0.67 ± 0.24* | 0.28* | 1.23 |
| 125 | 20 | 1.08 ± 0.34 | 0.50 | 2.08 |
| 300 | 20 | 1.70 ± 0.42 | 0.70 | 3.10 |

*Probability <0.05.

The preparation according to the present invention had an antiulcerous activity within a broad range of doses of from 5 to 50 μg/kg. The maximum effective was the dose of 12 μg/kg. A considerable increase of the preparation dose caused a reduced antiulcerous effect of the preparation.

In a separate series of experiments a comparative study of the effect of the preparation according to the present invention and cymethidin on the formation and progress of experimental duodenal ulcers. 170 rats were used. After administration of cystamine over several weeks the first group of animals were injected twice a day with the preparation according to the present invention in the maximum effective dose (12 μg/kg), the second group—cymethidin—in the dose of 7 mg/kg a day which corresponded to a standard dose used for the treatment of peptic ulcer in human beings. The animals of the control group were injected with a physiological solution. The slaughter of the animals was effected in groups of 10 animals within different periods after the beginning of the experiment. The obtained results are shown in Table 2.

TABLE 2

Variation of the ulcer index under the effect of the preparation of this invention and cymethidin

| Prepara- | Time | | | | | | |
|---|---|---|---|---|---|---|---|
| tion | 24 hrs* | 48 hrs | 72 hrs | 7 ds** | 14 ds | 21 ds | 28 ds |
| Control | 3.1 | 3.3 | 3.2 | 1.8 | 1.2 | 0.4 | 0 |
| Preparation of this invention | 1.4 | 0.4 | 0.6 | 0 | 0 | — | — |
| Cymethidin | 1.6 | 1.6 | 1.5 | 0.8 | 0 | | |

*hrs - hours,
**ds - days.

Therefore, a complete healing of ulcers under the effect of the preparation according to the present invention took place by the end of the 1-st week, while under the effect of cymethidin—by the end of the second week. After 48 hours the preparation according to the present invention caused a considerably greater reduction of the index as compared to cymethidin. The single dose of the preparation according to the present invention was by 600 times smaller than that of cymethidin.

Origination of gastric ulcers in rats was caused by immobilization for 24 hours in the dorsal position at the temperature of 25° C. Experiments were carried out with 120 male rats with a mass of 150-200 g. The animals were slaughtered by decapitation immediately on completion of the immobilization. The preparation according to the present invention was administered once subcutaneously 30 minutes after the beginning of immobilization. The intensity of erosio-ulcer injuries of the stomach was evaluated visually and expressed as a total of maximum length of all defects of the stomach mucous membrane (in mm). The test results are shown in Table 3 hereinbelow.

TABLE 3

Effect of the preparation according to the present invention on stomach cancer in rats

| Parameter | Control | Dose of the preparation, μg/kg | | |
|---|---|---|---|---|
| | | 1 | 12 | 125 |
| Number of animals | 30 | 30 | 30 | 30 |
| Intensity mm | 10.8 ± 1.8 | 3.2 ± 0.7* | 2.9 ± 0.7* | 4.7 ± 1.2* |

*Probability <0.05.

Therefore, the preparation according to the present invention substantially lowers the intensity of erosion-ulcer injuries of the stomach mucous membrane in rats upon immobilization thereof. The maximum activity of the preparation according to the present invention was revealed upon administration thereof in the dose of 12 μg/kg.

Upon slaughter of the animals blood was sampled from cervical vessels and in its serum the concentration of gastrin was determined. The results obtained are shown in Table 4.

TABLE 4

Effect of the preparation according to the present invention on concentration of gastrin in rats' blood serum

| No. | Parameter | Vivarium control | Test control | Preparation dose μg/kg | | |
|---|---|---|---|---|---|---|
| | | | | 1 | 12 | 125 |
| 1. | Number of animals | 20 | 30 | 30 | 30 | 30 |
| 2. | Gastrin, pg/ml | 46.8 ± 2.1 | 60.9 ± 3.9 | 51.8 ± 8.0 | 44.0 ± 4.6* | 60.2 ± 10.9 |

*Probability <0.05.

As it follows from the above Table 4 the preparation according to the present invention when administered in the dose of 12 μg/kg certainly lowers the level of gastrin which has been elevated in rats subjected to immobilization.

In experiments on 50 male rats the effect of the preparation according to the present invention on the production of hydrochloric acid by the stomach was studied. The rats' pylorus was preliminarily ligated, whereafter the preparation of this invention was subcutaneously administered in a single dose. The rats were slaughtered 1 hour afterwards, the amount of gastric juice was measured (in ml), as well as its acidity in titration units. The test results are shown in Table 5 hereinbelow.

TABLE 5

Effect of the preparation according to the present invention on secretion of hydrochloride acid in rats

| No. | Parameter | Control | Dose of the preparation, μg/kg | | |
|---|---|---|---|---|---|
| | | | 1 | 12 | 125 |
| 1. | Juice volume, ml | 1.97 ± 0.12 | 1.94 ± 0.37 | 0.87 ± 0.07 | 1.91 ± 0.47 |
| 2. | Acidity, titr. units | 46.8 ± 4.2 | 30.2 ± 2.6* | 32.5 ± 1.9* | 31.9 ± 2.3* |

*P <0.05.

Therefore, the preparation according to the present invention reduced acidity of the gastric juice in all doses without, however, changing the volume of gastric secretion.

The above experimental studies have shown a clearly pronounced protective effect of the preparation according to the present invention on the mucous membrane of the stomach and duodenum which causes its antiulcerous effect. This effect of the preparation according to the present invention is enhanced by its inhibiting action on secretion of gastrin and hydrochloric acid.

The study of toxicity of the preparation according to the present invention has shown a low toxicity upon a single administration of the preparation. The dose of the preparation causing death of 50% of white mice ($LD_{50}$) was 520 mg/kg (variation from 433 to 624 mg/kg) upon intravenous administration. IN V-star rats the $LD_{50}$ upon intravenous administration of the preparation was 270 mg/kg.

The chronical toxicity of the preparation according to the present invention was studied for 2 months on rats, rabbits and dogs; the preparation was administered daily in a single-time injection intramuscularly in the doses of 0.2 and 2.0 mg/kg to separate groups of animals of each species. No generally toxic effect was observed. No certain changes on the part of hematological and biochemical characteristics of blood, urina analyses were observed. The data of functional tests proved lack of changes in the function of lever, kidneys, thyroid gland and pancreas. No certain changes were observed in the level of sex hormones, adrenal cortex hormones.

The histological studies of liver, lungs, kidneys, heart, hypophysis, sexual glands of the animals administered with the preparation according to the present invention in the dose of 2 mg/kg (i.e. by 100 times higher than the purported therapeutic dose) have shown that the preparation causes no substantial morphological changes.

In the investigation of the mutagenous activity of the preparation according to the present invention on mice of the C 57 BL/6 line no increase of chromosomic injuries was revealed in cells of bone marrow of the mice which points to the absence of mutagenous activity in the preparation according to the present invention.

The preparation was tested in clinic on 40 patients suffering from duodenal peptic ulcer. The control groups consisted of 20 patients treated with cymethidin in the daily dose of 800 mg. Only male patients were subjected to the treatment, their age varied from 22 to 56 years. The duration of the disease was different: from newly detected ulcer to 28 years of the disease. The diagnosis of the peptic ulcer was made on the basis of generally accepted clinical tests with an obligatory use of the gastroduodenoscopy. The gastroduodenoscopy was carried out prior to administration of the preparation and 14, 21 and 28 days thereafter (the two latter endoscopy were carried out only in the use of non-scarring ulcers).

On the first day and 14 days after the administration of the preparation according to the present invention blood was taken for biochemical analyses, determination of the concentration of a number of hormones. At the same time, analyses of urine and stood were performed. During the gastroduodenoscopy biopsy was taken from the fundal and antral sections of the stomach, as well as from duodenum cap. At the beginning and at the end of administration of the preparation according to the present invention the secretory function of the stomach was studied with the assessment of the basal and pentagastrin-stimulated secretion of hydrochloric acid.

The preparation was administered intramuscularly in a dose of 10–15 μg/kg in a 0.9% aqueous solution of sodium chloride twice a day (in the moring at 7 a.m. and in the evening at 19 p.m.). The treatment course was 14–28 days, the course dose of the preparation was 30–60 mg. Apart from the preparation, the patients were given no additional pharmaceuticals, antacids were also excluded.

An average term of healing of the duodenal ulcer in the group of patients treated with the preparation according to the present invention was 22.8 days. By the end of the 2-nd week of the treatment the scarring of ulcer was found in 47.5% of the patients; by the end of the 3-rd week the ulcer healed in 85% of the patients; by the end of the fourth week the ulcer was not scarred only in one patient, i.e. healing took place in 97.5% of the cases.

In the patients treated with cymethidin in the dose of 200 mg 4 times a day by the end of the 3-rd week the healing of ulcer was observed in 65% of the patients which is essentially lesser a percentage than for the same period of treatment with the preparation according to the present invention (85%).

The treatment with the preparation according to the present invention accelerated disappearace of pains in the epigastric region characteristic for the peptic ulcer disease: on the 3-rd day pains disappeared in 50% of the patients, by the end of the 2-nd week of the treatment no pains were recorded in 97.5% of the patients. In the case of treatment with cymethidin by the end of the 2-nd week pains were still noted in 35% of the patients.

No clinically pronounced side phenomena were observed against the background of administration of the preparation according to the present invention, except for 2 patients who displayed a slight skin irritation which stopped after administration of antihistamine preparations without, however, canceling the preparation according to the present invention.

The administration of the preparation according to the present invention caused no essential deviations of the function of the cardio-vascular system: electrocardiogram, arterial pressure, heart's beat rate. In 3 patients with liability to the arterial hypertension normalization of the arterial pressure was observed against the background of administration of the preparation of this invention.

Analyses of gastric juice were carried out both before and after 2 weeks of administration of the preparation using the fraction method with the assessment of the basal production of hydrochloric acid and secretion in response to stimulation by an intramuscular single-time administration of pentagastrin in the dose of 5 μg/kg. The test results are shown in Table 6 hereinbelow.

TABLE 6

Secretion of hydrochloric acid prior to and after treatment with the preparation according to the present invention

| Parameter | Basal secretion | | Stimulated secretion | |
|---|---|---|---|---|
| | before treatment | after treatment | before treatment | after treatment |
| Juice volume, ml | 180.2 ± 19.1 | 115.3 ± 19.8* | 212.0 ± 14.1 | 198.6 ± 30.3 |
| Acid ejaculation, mequiv/h | 21.8 ± 1.4 | 10.6 ± 3.4* | 36.6 ± 3.3 | 36.1 ± 7.8 |

*Probability <0.05.

Therefore, the treatment with the preparation according to the present invention resulted in a reduction of the basal secretion of hydrochloric acid, providing no effect on the secretory response of the gastric glands to the stimulation by pentagastrin.

The study of hematological characteristics (hemoglobin, leukocytes, eosinophilic, neutrophilic leukocytes, lymphocytes, monocytes, ESR/erythrocyte sedimentation rate/) was effected weekly; the treatment with the preparation according to the present invention proved to be non-affecting the studied characteristics.

In the patients treated with the preparation according to the present invention once every two weeks the following characteristics were determined in blood: glucose, transaminases, amylase, alkali phosphatase, urea, creatinine, total protein, bilirubin, creatinphosphokinase, lactatedehydrogenase, cholinesterase, leucinaminopeptidase, gamma-glutamyltranspeptidase, glutamatedehydrogenase, potassium, calcium, sodium, chlorine. No certain changes of these parameters were noted against the background of the treatment with the preparation according to the present invention. In 3 patients there was noted a temporary increase in the activity of asparagic transaminase in blood which diappeared upon a repeated determination of the enzyme a week afterwards. Other characteristics characterizing the functional state of the liver were not changed in the 20 patients.

In 20 patients the basal concentration of a number of hormones was determined in plasma both prior to and after the treatment with the preparation according to the present invention using radioimmunological methods: gastrin, insulin, glucagon, growth hormone, adrenocorticotropic hormone, prolactin, thyrotropic hormone, thyroxin, triiodothyronine, follicle stimulating hormone, luteinizing hormone, aldosterone, hydrocortone, estradiol, progresterone and testosterone. Concentrations of all hormones in blood were not changed; only an uncertain increase of the basal level of insulin was observed (12.1±±0.67 μED/ml prior to the treatment, 16.7±2.2 μED/ml after the treatment).

Morphological studies were effected on 17 patients treated with the preparation according to the present invention. Biopsy was taken through an endoscope from an intact mucous membrane of the duodenum, from the antral and fundal sections of the stomach. The biopsy samples were fixed, sealed in paraffin. Serial sections with a thickness of 3–5 μm were dyed by hematoxylin-eosine and also by methods of immunocytochemical dyeing using specific antiserum towards gastrin I-17 (to reveal G-cells), towards somatostatin I-14 (for visualization of D-cells) and the complex peroxidase-antiperoxidase. The number of endocrinic cells was counted by means of a special screen on 1 mm$^2$ of the mucous membrane of the stomach and intestine. The results of calculations were compared with the characteristics obtained in an immunocytochemical analysis of biopsy samples taken from 12 persons of the control group (substantially healthy people).

The general morphological pattern prior to the treatment revealed an increased infiltration of the mucous membrane of the stomach and duodenum by lymphocytes and plasmatic cells, as well as a decreased mitotic index in the epithelium. After the treatment with the preparation according to the present invention in 53% of the patients an enhanced lympho-plasmacytic infiltration was observed as compared to the corresponding characteristics prior to the treatment, in 35% of the patients no changes were revealed, in 12% of the patients this infiltration was reduced. At the same time, almost double increase of the mitotic index was noticed which could point to more intensive processes of regeneration in the mucous membrane.

The variation of the number of endocrinic cells is shown in the following Table 7.

TABLE 7

Effect of the preparation according to the present invention on the number of endocrinic cells in the mucous membrane of the antral section of the stomach and duodenum

| Location | G-cells, per mm$^2$ | D-cells, per mm$^2$ |
| --- | --- | --- |
| Antral section of the stomach: | | |
| Control | 293 ± 27 | 53 ± 6 |
| Before treatment | 628 ± 92* | 38 ± 4 |
| After treatment | 400 ± 53 | 69 ± 6** |
| Duodenum: | | |
| Control | 39 ± 6 | 41 ± 5 |
| Before treatment | 48 ± 3 | 35 ± 4 |
| After treatment | 48 ± 3 | 39 ± 7 |

*Probability <0.05 relative to the control;
**Probability <0.05 relative to the characteristics before the treatment.

Therefore, against the background of the treatment with the preparation according to the present invention there occurs a reduction of an increased number of G-cells producing gastrin which is combined with an increase of the reduced number of D-cells producing somatostatin.

Clinical tests of the preparation according to the present invention have shown its high effectiveness in respect of healing of duodenal ulcer which is superior over that of cymethidin. The preparation according to the present invention contributes to a rapid disappearance of the pain syndrome lowers the basal secretion of hydrochloric acid, intensifies regeneration processes in the gastroduodenal mucous membrane (according to the data of the mitotic index determination). The preparation according to the present invention is nontoxic, does not affect functions of the most important visceral organs, causes no changes in the blood characteristics, does not affect endocrinic glands.

The preparation according to the present invention can be used in various pharmaceutical forms, namely in the form of injectionable solutions, tablets, suppositoria. It is also possible to use the intranasal mode of its administration. When administered in the form of injectionable solutions, the latter contain 0.1–0.5% by weight of the active ingredient. The injectable solution is administered in the dose of 1 ml 2–3 times a day.

As the solvent use is made of bidistilled water, a 0.9% aqueous solution of sodium chloride, Ringer's solution, a solution of glucose.

The pharmaceutical preparation according to the present invention in the form of tablets and suppositoria preferably contains the active principle in an amount of 10 to 50 mg per tablet or suppositorium. For suppositoria any pharmaceutically acceptable vehicle can be used, for tablets as the pharmaceutical vehicle it is preferred to use starch, glucose, lactose.

The preparation is administered in a dose of 1–2 tablets 3 times a day before meals. The course of treatment with the preparation according to the present invention takes 14 to 28 days. The preparation according to the present invention has no side effects or contrainidications to its administration. Ready pharmaceutical forms of the preparation according to the present invention are produced by conventional processes. The active principle of the preparation of this invention can be synthesized by standard procedures of the peptide chemistry, for example by the method of a step-wise propagation of a peptide chain, starting from the C-terminal free arginine, by means of activated esters of substituted aminoacids through the following intermediate compounds: carbobenzoxy-leucyl-arginine; carbodenzoxy-phenylalanyl-leucyl-arginine; carbobenzoxy-glycyl-phenylalanyl-arginine; carbodenzoxy-D-alanyl-glycol-phenylalanyl-leucyl-arginine; carbobenzoxy-O-benzyl-tyrozyl-D-alanyl-glycyl-phenylalanyl-leucyl-arginine.

INDUSTRIAL APPLICABILITY

The preparation according to the present invention is useful in the gastroenterology as a pharmaceutical preparation for the treatment of the peptic ulcer disease.

We claim:

1. A process for the treatment of peptic ulcer in a warm blooded animal which comprises administering to said warm blooded animal an anti-peptic ulcer effective amount of a peptide of the following structure:

Tyr-D-Ala-Gly-Phe-Leu-Arg in a pharmaceutically acceptable carrier.

2. A process for the treatment of peptic ulcers in a warm blooded animal which comprises administering to said warm blooded animal a pharmaceutically acceptable amount of the preparation of claim 1, an injectable solution containing as the active ingredient said peptide in an amount of from 0.1 to 0.5% by weight.

3. A process for the treatment of peptic ulcers in a warm blooded animal which comprises administering to said warm blooded animal a pharmaceutically acceptable amount of the preparation of claim 1, wherein said carrier is bidistilled water.

4. A process for the treatment of peptic ulcers in a warm blooded animal which comprise administering to said warm blooded animal a pharmaceutically acceptable amount of the preparation of claim 1, wherein said carrier is a 0.90% aqueous solution of sodium-chloride.

5. A process for the treatment of peptic ulcers in a warm blooded animal which comprises administering to said warm blooded animal a pharmaceutically acceptable amount of the preparation of claim 1, wherein said preparation is in the form of tablets and contains as the active ingredient said peptide in an amount of 10 to 50 mg per tablet.

6. A process for the treatment of peptic ulcers in a warm blooded animal which comprises administering to said warm blooded animal a pharmaceutically acceptable amount of the preparation of claim 1, wherein said preparation contains as a pharmaceutically acceptable carrier, a filler selected from the group consisting of starch, glucose or lactose.

* * * * *